United States Patent [19]

Raven

[11] Patent Number: 5,019,374
[45] Date of Patent: May 28, 1991

[54] DENTIFRICES

[75] Inventor: Stephen J. Raven, Wirral, Great Britain

[73] Assignee: Chesebrough-Pond's USA Co., Division of Conopco, Inc., Greenwich, Conn.

[21] Appl. No.: 470,024

[22] Filed: Jan. 25, 1990

[30] Foreign Application Priority Data

Jan. 25, 1989 [GB] United Kingdom ............... 8901587

[51] Int. Cl.$^5$ ........................... A61K 7/16; A61K 7/18
[52] U.S. Cl. .......................................... 424/52; 424/57
[58] Field of Search ............................ 424/49, 52, 57

[56] References Cited

U.S. PATENT DOCUMENTS

| | | | |
|---|---|---|---|
| 3,699,220 | 10/1972 | Westrate et al. | 424/57 |
| 3,864,471 | 2/1975 | King et al. | 424/52 |
| 3,927,201 | 12/1975 | Baines et al. | 424/57 |
| 3,927,202 | 12/1975 | Harvey et al. | 424/57 |
| 4,132,773 | 1/1979 | Best et al. | 424/57 |
| 4,152,419 | 5/1979 | Pensak | 424/52 |
| 4,247,526 | 1/1981 | Jarvis et al. | 424/57 |
| 4,340,583 | 7/1982 | Wason | 424/49 |
| 4,374,823 | 2/1983 | Harvey et al. | 424/49 |
| 4,394,371 | 7/1983 | Barberio | 424/49 |
| 4,460,565 | 7/1984 | Westrate et al. | 424/52 |
| 4,894,220 | 1/1990 | Nabi et al. | 424/49 |
| 4,913,895 | 4/1990 | Miyake et al. | 424/49 |
| 4,933,171 | 6/1990 | Bristow et al. | 424/49 |

FOREIGN PATENT DOCUMENTS 2102289  2/1963  United Kingdom .

*Primary Examiner*—Shep K. Rose
*Attorney, Agent, or Firm*—Milton L. Honig

[57] ABSTRACT

The invention relates to a toothpaste which contains a mixture of an alkalimetal trimetaphosphate and a fluoride salt as anti-caries agents. The interaction between the trimetaphosphate salt and the fluoride salt is substantially reduced by providing the trimetaphosphate salt to be present in the liquid phase of the toothpaste in at least partly insoluble form. Optimum results are obtained if all the trimetaphosphate is present in insoluble form in the liquid phase.

4 Claims, No Drawings

DENTIFRICES

This invention relates to dentifrices, more particularly toothpaste compositions.

Toothpaste compositions usually comprise as the main constituents a solid phase consisting primarily of a finely-divided solid particulate abrasive cleaning agent and a liquid phase mainly constituted by humectant and water. The solid phase is maintained homogeneously and stably dispersed in the liquid phase with the aid of a so-called binder.

Most toothpastes marketed at the present time also comprise one or more compounds to improve the health of the oral cavity in some way. Of these, very considerable use is made of agents for inhibiting dental caries. For this purpose a water-soluble fluoride salt releasing the $F^-$ ion in water, especially sodium fluoride, is widely used. Among other anti-caries agents that have been proposed for use in toothpaste are trimetaphosphate (TMP) alkalimetal salts. The most well known of these is sodium trimetaphosphate, a water-soluble cyclic condensed phosphate of the formula $Na_3P_3O_9$. US-A-4 132 733 (Best et al) and US-A-3 699 220 (Weststrate et al) describe toothpaste formulations containing a trimetaphosphate salt in an amount of up to 20%.

We believe that a particularly useful anti-caries toothpaste results from combining in one product a fluoride salt and a TMP salt. However, we have discovered that when this is done a chemical interaction occurs between the fluoride ion and the TMP ion with the result that there is a substantial loss of the active therapeutic agents, water-soluble fluoride and TMP, on storage of the toothpaste.

The present invention is concerned with mitigating the stability problem due to the potential, during storage of a toothpaste, of reaction occurring between the TMP ion and another toothpaste ingredient, especially a second therapeutic agent, such as the fluoride ion. Our investigations have shown that an effective therapeutic toothpaste having improved stability is obtained if the TMP salt is in at least partly insoluble form in the liquid phase of the toothpaste.

According to the present invention there is provided a method of making a toothpaste which comprises mixing an effective anti-caries amount of TMP salt and another toothpaste ingredient reactive with the TMP salt with other solid and liquid ingredients, wherein the ingredients of the toothpaste are chosen so that when the TMP salt is combined with all the water soluble, water miscible and aqueous ingredients of the toothpaste and the mixture equilibrated, as more particularly described hereinafter and referred to as the TMP solubility test, less than 80% of the TMP salt is dissolved.

The effective anti-caries amount of TMP salt may range from 0.01 to 20%, preferably from 0.2 to 15% by weight of the total toothpaste.

The amount of TMP salt which dissolves in the TMP solubility test is strongly influenced by the nature and amount of the humectant component of the toothpaste.

The humectants most commonly used in toothpastes are glycerol and 70% sorbitol solution, the latter generally being referred to as sorbitol syrup. TMP salts are less soluble in glycerol than in sorbitol syrup. The humectant of the toothpaste prepared according to this invention desirably comprises at least 50% by weight of sorbitol syrup or at least 40% by weight of glycerol, more preferred amounts being, respectively, 60% and 50% by weight. This invention is not of course limited to the use of glycerol and/or sorbitol syrup as humectants but others may also be used. However, since, as noted above, glycerol and sorbitol syrup are extremely widely used in practice in the manufacture of toothpastes the following discussion will concentrate mainly on their use.

It has also been found that the proportion of the TMP salt which is dissolved in the TMP solubility test can be decreased by employing toothpaste ingredients which increase the non-ionic nature of the liquid phase of the toothpaste. Such ingredients include polyethyleneglycols and lower aliphatic alcohols, particularly ethanol. A mixture of a polyethylene glycol and a lower aliphatic alcohol may also be used. Solid or liquid polyethylenegoycols may be employed. Another ingredient which is useful for the same purpose is urea. The toothpaste may comprise amounts of about 1% to about 20% by weight of such ingredients.

Preferred toothpastes of the invention are those for which, in the TMP solubility test, the proportion of the TMP salt dissolved is substantially less than 80%, such as less than 50%, particularly less than 25%. In more preferred toothpastes this amount is less than 10%, optimum stability being obtained when the amount is substantially 0%.

The TMP solubility test referred to above is carried out as follows. The TMP salt is combined with all the water miscible, water soluble and aqueous ingredients of the toothpaste. The mixture is agitated and left at ambient temperature (about 25° C.) for 16 hours to equilibrate. The mixture is then centrifuged and the supernatant liquid collected. The liquid phase is then analysed for TMP using ion exchange chromatography. The method of this invention relates to the manufacture of toothpastes whose ingredients are so selected that in this test less than 80% of the TMP salt is present in the supernatant liquid.

In one embodiment of the method of the invention the toothpaste ingredient reactive with the TMP salt is a second therapeutic agent, preferably a source of fluoride ions which may be any phsiologically acceptable fluoride salt. Many such salts for inclusion in toothpastes have been proposed in the literature. Especially preferred is sodium fluoride.

Toothpastes made according to the invention will usually comprise a particulate solid abrasive cleaning agent. Commonly used abrasive agents include silica, alumina, hydrated alumina, calcium carbonate, anhydrous dicalcium phosphate, dicalcium phosphate dihydrate and water-insoluble sodium metaphosphate. The amount of abrasive agent is usually between 5% and 70% by weight of the toothpaste.

As noted above commonly used humectants are glycerol and sorbitol syrup (usually comprising an approximately 70% solution). However, other humectants are known to those in the art including propylene glycol, lactitol, xylitol and hydrogenated corn syrup. In toothpastes made according to the method of this invention the amount of the humectant exceeds that used in making known TMP-containing toothpastes and generally ranges up to about 85% weight of the toothpaste.

Numerous binding or thickening agents have been indicated for use in toothpastes, preferred ones being hydroxyethylcellulose, sodium carboxymethylcellulose and xanthan gum. Others include natural gum binders such as gum tragacanth, gum karaya and gum arabic, Irish moss, alginates and carrageenans. Silica thickening agents include the silica aerogels and various precipitated silicas. Mixtures of binders and thickening agents may be used. The amount of binder included in a dentifrice is generally between 0.1% and 10% by weight.

It is usual to include a surfactant in a toothpaste and again the literature discloses a wide variety of suitable materials. Surfactants which have found wide use in practice are sodium lauryl sulphate, sodium dodecylbenzene sulphonate and sodium laurolylsarcosinate.

Other anionic surfactants may be used as well as other types such as cationic, amphoteric and non-ionic surfactants. Surfactants are usually present in an amount of from 0.5% to 5% by weight of the toothpaste.

Flavours that are usually used in toothpastes are those based on oils of spearmint and peppermint. Examples of other flavouring materials used are menthol, clove, wintergreen, eucalyptus and aniseed. An amount of from 0.1% to 5% by weight is a suitable amount of flavour to incorporate in a toothpaste.

In the method of the invention there may be used a wide variety of optional toothpaste ingredients. These include a monofluorophosphate as a further anti-caries agent, such as sodium monofluorophosphate; a sweetening agent such as saccharin; an opacifying agent, such as titanium dioxide; a preservative, such as formalin; a colouring agent; -or pH controlling agent such as an acid, base or buffer, such as sodium hydroxide. Antibacterial agents such as 2', 4,4'-trichloro-2-hydroxydiphenyl ether may also be included.

For a fuller discussion of the formulation of toothpaste compositions reference is made to Harry's Cosmeticology, Seventh Edition, 1982, Edited by J B Wilkinson and R J Moore, pages 609 to 617.

The pH of toothpastes made according to the invention are desirably about 4 to about 10. In those cases where there is a substantial amount of the TMP dissolved in the solubility test the pH is preferably at least 6.

Toothpastes produced according to the invention are used in the conventional way. When introduced into the mouth the insoluble TMP salt dissolves in the oral fluids becoming available to exert a therapeutic effect.

The following Examples illustrate the invention. Percentages are by weight.

EXAMPLE 1

A toothpaste is made from the following ingredients by a conventional mixing procedure.

| Ingredient | % |
| --- | --- |
| Silica xerogel (abrasive) | 10.00 |
| Precipitated silica (thickener) | 10.00 |
| Glycerol | 58.00 |
| Polyethyleneglycol 1500 | 5.00 |
| Sodium carboxymethylcellulose | 0.50 |
| Sodium lauryl sulphate | 1.50 |
| Sodium trimetaphosphate | 3.00 |
| Sodium fluoride | 0.154 |
| Sodium saccharin | 0.05 |
| Sodium hydroxide | 0.05 |
| Trisodium orthophosphate | 0.06 |
| Titanium dioxide | 1.00 |
| Flavour | 1.00 |
| Demineralised water | to 100.00 |

In carrying out the TMP solubility test, the sodium trimetaphosphate is combined with all the water miscible, water soluble and aqueous ingredients, i.e. all the ingredients except the two silicas, the sodium carboxymethylcellulose, the titanium dioxide and the flavour. When carrying out the test less than 80% of the sodium trimetaphosphate dissolves.

EXAMPLE 2

A toothpaste is made as in Example 1 except that 55.00 g of glycerol are used and 5% of the water is replaced by the same weight of ethanol.

EXAMPLE 3

A toothpaste is made as in Example 1 except that the amount of glycerol is 48.00 g.

EXAMPLE 4

A toothpaste is made as in Example 1 except that the 10.00 g of the glycerol are replaced by 10.00 g sorbitol syrup (70% solution).

EXAMPLE 5

A toothpaste is made as in Example 1 except that the amount of sodium fluoride is 0.11 g.

EXAMPLE 6

A toothpaste is made as in Example 1 except that the amount of sodium fluoride is 0.22 g.

EXAMPLE 7

A toothpaste is made as in Example 1 except that the amount of sodium fluoride is 0.33 g.

In the case of each of Examples 2 to 7 the proportion of sodium trimetaphosphate dissolved in the TMP solubility test is less than 80%.

The extent of the interaction of the fluoride ion and the TMP ion can be monitored by measuring the concentration of either ion. However, loss of fluoride ion is easier to determine than loss of TMP ion.

We have performed experiments in which various humectant liquids were combined with an amount of NaF corresponding to 2100 ppm F and 4.6% TMP and stored at 25° C. for six weeks. These showed, that the $F^-$ concentration, and therefore TMP stability, was greater when the humectant was 100% sorbitol syrup than when it comprised a 50% solution in water of sorbitol syrup, and greater when it comprised a 60% solution in water of glycerol than when it comprised 30% glycerol.

In another experiment it was shown that 4.1% sodium trimetaphosphate is about the maximum amount that can be dissolved in a 40% solution in water of sorbitol syrup, or in a 30% solution in water of glycerol, at 25° C.

EXAMPLE 8

Several toothpaste, the formulation of which is given below, were stored at different temperatures for 3 months. The residual fluoride and TMP were measured. The results are given below.

| | A | B | C | D | E | F | G |
| --- | --- | --- | --- | --- | --- | --- | --- |
| Silica xerogel | 10.00 | 10.00 | 10.00 | 10.00 | 10.00 | 10.00 | 10.00 |

-continued

| | A | B | C | D | E | F* | G* |
|---|---|---|---|---|---|---|---|
| precipitated silica | 10.00 | 10.00 | 10.00 | 10.00 | 10.00 | 10.00 | 10.00 |
| glycerol | 58.00 | 53.00 | 48.00 | 58.00 | 48.00 | — | 55.00 |
| polyethyleneglycol 1500 | 5.00 | 5.00 | 5.00 | 5.00 | 5.00 | 5.00 | 5.00 |
| sodium carboxymethylcellulose | 0.50 | 0.50 | 0.50 | 0.50 | 0.50 | 0.50 | 0.50 |
| titanium dioxide | 1.00 | 1.00 | 1.00 | 1.00 | 1.00 | 1.00 | 1.00 |
| sodium laurylsulphate | 1.50 | 1.50 | 1.50 | 1.50 | 1.50 | 1.50 | 1.50 |
| saccharin | 0.30 | 0.30 | 0.30 | 0.30 | 0.30 | 0.30 | 0.30 |
| sodium fluoride | 0.22 | 0.22 | 0.22 | 0.33 | 0.33 | 0.33 | 0.33 |
| trisodium orthophosphate | 0.06 | 0.06 | 0.06 | 0.06 | 0.06 | 0.06 | 0.06 |
| sodium hydroxide | 0.07 | 0.07 | 0.07 | 0.07 | 0.07 | 0.07 | 0.07 |
| sodium trimetaphosphate | 3.00 | 3.00 | 3.00 | 3.00 | 3.00 | 3.00 | 3.00 |
| ethanol | — | — | — | — | — | — | 5.00 |
| flavour | 1.00 | 1.00 | 1.00 | 1.00 | 1.00 | 1.00 | 1.00 |
| sorbitol | — | — | — | — | 10.00 | 68.00 | — |
| demineralised water | to 100→ | | | | | | |

Storage data: ppm F/% TMP

| | A | B | C | D | E | F* | G* |
|---|---|---|---|---|---|---|---|
| 6° C. | 1023 3.0 | 927 3.0 | 905 3.0 | 1459 2.7 | 1335 3.4 | 816 2.1 | 1396 3.0 |
| 20° C. | 1021 2.9 | 908 2.9 | 900 2.5 | 1397 3.0 | 1289 3.0 | 804 2.0 | 1382 2.8 |
| 37° C. | 1121 2.7 | 869 2.7 | 921 2.7 | 1236 2.4 | 1066 1.9 | 530 1.4 | 1298 2.8 |

*stored only for 2 months

A and C had a residual F concentration of 960 and 860 respectively after storage at 20° C. for 12 months.

I claim:
1. A toothpaste comprising:
   (i) a finely-divided solid particulate abrasive present in an effective amount for abrasively cleaning teeth;
   (ii) sodium trimetaphosphate present in an effective amount for anti-caries protection;
   (iii) sodium fluoride present in an effective amount when combined with said sodium trimetaphosphate to deliver anti-caries protection; and
   (iv) a liquid phase within which is stably dispersed said solid particulate abrasive, said liquid phase comprising from about 1 to about 20% by weight of ingredients selected from the group consisting of polyethylene glycols, lower aliphatic alcohols, urea and mixtures thereof, and a humectant selected from the group consisting of glycerol present in at least 40% by weight of the toothpaste and sorbitol syrup present in at least 50% by weight of the toothpaste, and said sodium trimetaphosphate which is present being dissolved in said liquid phase in amounts less than 80% of total amount of sodium trimetaphosphate in the toothpaste, while a remainder of said sodium trimetaphosphate is present in undissolved form in said liquid phase.

2. A toothpaste according to claim 1, wherein the amount of dissolved trimetaphosphate is less than 25%.

3. A toothpaste according to claim 1, wherein the amount of dissolved trimetaphosphate is less than 10%.

4. A toothpaste according to claim 1, wherein the amount of dissolved trimetaphosphate is 0%.

* * * * *